(12) United States Patent
Vilsmeier

(10) Patent No.: US 6,484,047 B1
(45) Date of Patent: Nov. 19, 2002

(54) CONTINUOUS DETECTION AND ANALYSIS OF TISSUE CHANGES

(76) Inventor: Stefan Vilsmeier, Oberer Stadtplatz 6, 6330 Kufstein (AT)

( * ) Notice: Subject to any disclaimer, the term of this patent is extended or adjusted under 35 U.S.C. 154(b) by 0 days.

(21) Appl. No.: 09/671,717

(22) Filed: Sep. 27, 2000

(30) Foreign Application Priority Data

Sep. 28, 1999 (DE) .......................................... 199 46 429

(51) Int. Cl.⁷ ................................................. H61B 5/05
(52) U.S. Cl. ....................... 600/407; 382/128; 382/173; 382/294
(58) Field of Search ................................ 382/128, 173, 382/294; 600/407

(56) References Cited

U.S. PATENT DOCUMENTS

| | | |
|---|---|---|
| 4,722,056 A | 1/1988 | Roberts et al. |
| 5,383,454 A | 1/1995 | Bucholz |
| 5,389,101 A | 2/1995 | Heilbrun et al. |
| 5,411,026 A | 5/1995 | Carol |
| 5,603,318 A | 2/1997 | Heilbrun et al. |
| 5,768,413 A * | 6/1998 | Levin et al. ................. 382/173 |
| 5,779,634 A | 7/1998 | Ema et al. |
| 5,836,954 A | 11/1998 | Heilbrun et al. |
| 5,851,183 A | 12/1998 | Bucholz |
| 5,926,568 A * | 7/1999 | Chancy et al. ............... 382/217 |
| 5,974,159 A * | 10/1999 | Lubin et al. ................. 382/106 |
| 6,226,418 B1 * | 5/2001 | Miller et al. ................. 382/294 |

FOREIGN PATENT DOCUMENTS

| | | |
|---|---|---|
| DE | 197 26 226 A1 | 12/1998 |
| DE | 198 29 230 A1 | 3/2000 |

* cited by examiner

Primary Examiner—Marvin M. Lateef
Assistant Examiner—Jeoyuh Lin
(74) Attorney, Agent, or Firm—Renner, Otto Boisselle & Sklar, LLP

(57) ABSTRACT

A method of detecting tissue changes includes the following steps: a) taking a tissue structure scan for at least one part of a patient's body and all of the tissue structure scan data is stored; b) after a predetermined period of time, taking another tissue structure scan for at least that part of the patient's body at least once, and again storing the data; c) computer-assisted positional assignment and comparison of two or more sequential tissue structure scans; and d) computer-assisted detection and output of changes in the tissue of the patient, resulting from the different data for each body portion assigned.

20 Claims, No Drawings

CONTINUOUS DETECTION AND ANALYSIS OF TISSUE CHANGES

BACKGROUND OF THE INVENTION

1. Technical Field

The present invention relates to a method of detecting tissue changes.

Early recognition of tissue changes is vital in the medical field, especially in combating cancer since if tissue changes are ascertained relatively early on, in most cases, it is possible to take measures which lead to the complete recovery of the patient.

2. Description of Related Art

Known methods of early recognition are obtaining samples of body fluids for analysis, the scanning of tomographs, or in apparatus medicine also the observation, of tomographs as well as ultrasound images of individual body parts.

The disadvantage of all of these methods is that they can only furnish "moment images". Although, the physician is able to recognize the momentary condition of the tissue, he has no possibility of determining the growth of such a tissue change. Even for skilled physicians it is often difficult to pin-point diseased tissue changes from such a single image.

SUMMARY OF THE INVENTION

It is thus an object of the present invention to provide a method of detecting tissue changes which overcomes the aforementioned disadvantages. In particular, it is intended that changes in the shape and size of such tissue changes may be easily detected. The surgeon should be provided with technical means by means of which he can easily analyze the progress or formation of tissue changes.

For this purpose, the invention makes available a method of detecting tissue changes comprising the following steps:

a) taking a tissue structure scan for at least one part of a patient's body and storing all tissue structure scan data;

b) after a predetermined period of time, taking another tissue structure scan for the part or all of the patient's body at least once, and again storing the data;

c) computer-assisted positional assignment and comparison of the data of two or more sequential tissue structure scans;

d) computer-assisted detection and output of changes in the tissue of the patient, resulting from the different data of each body portion assigned.

In other words, either a body part or all of the patient's body is scanned for signs of a tissue change in defined periods of time over a lengthy time period. Once the computer has assigned and compared the matching body parts, any tissue changes can be ascertained and be output so that they are easily recognizable. Thus, it is possible to locate early a diseased site, forming or growing in the body, and to observe its development.

DETAILED DESCRIPTION OF THE PREFERRED EMBODIMENTS

When, in accordance with an embodiment of the invention, a whole body scan is done, there is no longer the risk of a relatively young diseased site being overlooked, and therapy can be instituted at an early stage. The assignment of the individual points on the body and comparison of two scans performed in sequence is handled by the computer, and since the tissue structure changes can be output by simple visible means, any diseased lesion, possibly in existence, can be recognized even by lesser skilled physicians.

Consequently, extensive early recognition is facilitated, thereby drastically improving the chances of recovery, especially in the case of cancer.

The tissue structure scan may be a tomography, on the one hand it could be a computer tomography or, on the other hand, it could also be a nuclear spin tomography. Furthermore, the tissue structure scan may also be a scan done in the field of nuclear medicine, a bone scintigraphy, a mammography, an ultrasound scan, a PET or a SPECT scan. In principle, all scans and medical diagnostic scans, which provide an image of tissue structure, are conceivable for use. Of course, the data obtained from all of the scanning methods cited above may be combined to guarantee a scan of the patient which is as complete as possible.

Using nuclear spin tomography is of particular advantage. Since the method in accordance with the invention is based on repeated scanning of the patient's body either completely or partially at specific time intervals, care must be taken to ensure that the radiation exposure is kept to a minimum. Nuclear spin tomography permits such a scanning with low radiation exposure, and more recently has become achievable with less complication.

Preferably, comparing the assigned tissue data in accordance with the invention is done by subtraction of the image data from the various scans, an image processing program may be used for this purpose.

In accordance with a particularly preferred embodiment of the method in accordance with the invention, the tissue changes are output visibly and distinguishable on a display after comparison, it being, for example, of advantage to emphasize with color the conspicuous tissue changes. The unchanged body parts are output transparent or semi-transparent so that the tissue changes and their positions are clearly discernible.

For this purpose, use is made preferably of a three-dimensional animation of the body. Such an output results in a "glass person", in which only the changed tissue locations are rendered visible, for example, by being emphasized with color. Even a relatively inexperienced medical practitioner is able to recognize diseased tissue lesions in such an image and monitor their growth. It is, of course, also possible to display, in addition to the emphasized tissue changes, semi-transparent fixed points in the body, for example the bone skeleton, to simplify localization.

Advantageously, the positional data of the tissue changes existing due to the scan(s) can be used for localization in subsequent treatments.

The positional assignment of the data from various tissue structure scans occurs in an embodiment in accordance with the invention by modeling the volume of the scanned body portion as a piece of elastic material, virtual external deforming forces being applied to the shape of the elastic piece of material until it matches the scanned body portions to be assigned, whereby the scan data sets may be firstly oriented globally.

Furthermore, the virtual external deforming forces are applied until equilibrium exists between the external forces and the internal reaction forces, the deformation progressing in a coarse-to-fine strategy until the external forces assume a minimum.

An embodiment of the method in accordance with the invention has essentially the following order of events:

The patient proceeds to a physician or some other facility where a nuclear spin tomograph is available. By the first scan, the entire body of the patient or a part thereof is scanned by means of nuclear spin tomography and the data is stored. It may happen that diseased tissue lesions are already detected by this first scan and this data may be used for further observation or already for initial treatment.

After a certain length of time, which, in the case of a healthy body, may amount to roughly half a year, and which is correspondingly shortened when there is a suspicion that diseased tissue changes exist, the patient returns for tomography and a second scan is made.

This is followed by computer-assisted comparison of the data and scanning and output of the tissue changes. This may be done by passing on the patient data to a central facility which has suitable computer systems, or in situ immediately after the tomograph scan if suitably equipped.

The data, about the patient's body, obtained from the two tomograph scans, are first of all positionally assigned. This means that the two images are first of all superimposed so that each of the body points in the first data set are assigned to the corresponding body points in the second data set. Such an assignment may be carried out, e.g., as follows:

An earlier image set of a patient is morphed with an updated image set, it being assumed that all human body parts exhibit the same topological structure, at least to a certain degree of representation, but may change in shape details as is the case, for example, with a growing tumor.

Firstly, two image sets are globally oriented for a rigid image registration using an algorithm. After this global orientation, the volume taken up by one of the image sets is modeled like a piece of elastic material. By applying external forces, the shape of the elastic object can be changed until it is adapted to the shape of the reference object. As a result of these forces, the object is deformed until equilibrium is achieved between the external forces and the inner resilient restoring forces. The deformation progresses in a coarse-to-fine strategy, enhancing the local adaptation and the global coherence.

Derivation of the external forces is the crux of the elastic adaptation model, these forces having the task of bringing like regions in the two image sets to match. The mutual exchange of information in this case is the suitable means for measuring the local degree of adaptation.

The problem in producing elastic matches may be formulated as an optimization problem of the cost function "costs =deformation −degree of adaptation". The task is thus to find external forces at which the cost function becomes a minimum. Shifting every point of the object is regulated by a coupled set of partial differential equations encompassing the external forces and a few parameters describing the elastic behavior of the model. These partial differential equations may be solved with the aid of a finite element method, taking into consideration the three-dimensional discretization in volume elements (voxels). The cited coarse-to-fine strategy reduces the computational time and reduces the risk of convergence to a local minimum.

Once the two data sets from the tomograph scans have been assigned, a comparison of the discrete portions is implemented, likewise computer-assisted. The data exhibiting no change is subtracted so that only the changes and their positions are visible. By using suitable filters, any changes which are definitely not due to disease can be ignored so that, upon conclusion of morphing, an animated complete body image of the patient can be displayed in which only suspected tissue changes are discernible. One major advantage afforded by this method is that also the growth of such tissue changes is now visible. Even slowly growing, very young cancerous tumors can be diagnosed and treated early, thus greatly improving the chances of recovery.

In order to prevent or to monitor the progress of treated and untreated tissue changes, the procedure described above is repeated at predetermined intervals.

In the foregoing description, preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A method of detecting tissue changes comprising the following steps:
    a) taking a volumetric tissue structure scan for at least one part of a patient's body and storing the volumetric tissue structure scan data;
    b) after a predetermined period of time, taking another volumetric tissue structure scan for the part or all of the patient's body at least once, and again storing the data;
    c) positionally assigning the data of two or more sequential tissue structure scans with the assistance of a computer, and comparing the volumetric tissue structure scan data;
    d) computer-assisted detection and output of volumetric changes in the tissue of the patient, resulting from the different data for each body portion assigned.

2. The method as set forth in claim 1, wherein the tissue structure scan is a tomography, in particular a computer tomography or a nuclear spin tomography.

3. The method as set forth in claim 1, wherein the tissue structure scan is a scan from the field of nuclear medicine, a bone scintigraphy, a mammography, an ultrasound scan, a PET or a SPECT scan.

4. The method as set forth in claim 1, wherein the data obtained from the scans includes data from different types of scan.

5. The method as set forth in claim 1, wherein the comparison is made by subtracting the data from various scans.

6. The method as set forth in claim 1, wherein, after comparison, the conspicuous tissue changes are output clearly visible and distinguishable on a display.

7. The method as set forth in claim 6, wherein the conspicuous tissue changes are emphasized with color.

8. The method as set forth in claim 6, wherein the unchanged body portions are outputted transparently or semi-transparently so that the tissue changes and their positions are clearly discernible.

9. The method as set forth in claim 1, wherein the output occurs as a three-dimensional animation of the body or the body part.

10. The method as set forth in claim 1, wherein the positional data of the tissue changes are used for localization in subsequent treatments.

11. The method as set forth in claim 1, wherein the positional assignment of the data from various tissue structure scans occurs by modeling the volume of the scanned body portion as a piece of elastic material, virtually external deforming forces being applied to the shape of the elastic piece of material until it matches the scanned body portions to be assigned.

12. The method as set forth in claim 11, wherein the data sets obtained from the scans are firstly oriented globally.

13. The method as set forth in claim 11, wherein the virtually external deforming forces are applied until equilibrium exists between the external forces and the internal reaction forces.

14. The method as set forth in claim 11, wherein the deformation progresses in a coarse-to-fine strategy until the external forces assume a minimum.

15. A method of detecting tissue changes, comprising the steps of:
  obtaining the data of two or more volumetric tissue structure scans taken at different times;
  positionally assigning the data of said two or more volumetric tissue structure scans with the assistance of a computer, and comparing the volumetric tissue structure scan data;
  computer-assisted detection and output of volumetric changes in the tissue of the patient, resulting from the different data.

16. The method as set forth in claim 15, wherein the positional assignment of the data from various tissue structure scans occurs by modeling the volume of the scanned body portion as a piece of elastic material, virtually external deforming forces being applied to the shape of the elastic piece of material until it matches the scanned body portions to be assigned.

17. The method as set forth in claim 16, wherein the virtually external deforming forces are applied until equilibrium exists between the external forces and the internal reaction forces.

18. The method as set forth in claim 16, wherein the deformation progresses in a coarse-to-fine strategy until the external forces assume a minimum.

19. The method as set forth in claim 16, further comprising globally orienting the data sets obtained from the scans.

20. The method as set forth in claim 15, wherein the comparison is made by subtracting the data from at least one of the scans.

* * * * *